(12) United States Patent
Shen et al.

(10) Patent No.: US 6,730,802 B2
(45) Date of Patent: May 4, 2004

(54) SILICON CARBIDE PRECURSOR

(75) Inventors: Qionghua Shen, Latham, NY (US); Leo Spitz MacDonald, Schenectady, NY (US)

(73) Assignee: Starfire Systems, Inc., Malta, NY (US)

( * ) Notice: Subject to any disclaimer, the term of this patent is extended or adjusted under 35 U.S.C. 154(b) by 0 days.

(21) Appl. No.: 10/191,912

(22) Filed: Jul. 9, 2002

(65) Prior Publication Data

US 2004/0063984 A1 Apr. 1, 2004

(51) Int. Cl.$^7$ .................................................. C07F 7/08
(52) U.S. Cl. ........................ 556/12; 556/431; 556/435; 556/480; 438/778; 427/96
(58) Field of Search .......................... 556/12, 431, 435, 556/480; 438/778; 427/96

(56) References Cited

U.S. PATENT DOCUMENTS

| 5,075,477 A |   | 12/1991 | Jung |
| 5,153,295 A | * | 10/1992 | Whitmarsh et al. ........... 528/31 |
| 6,225,238 B1 | * | 5/2001 | Wu ............................. 438/778 |

OTHER PUBLICATIONS

Bacque et al, J. Of Organometallic Chemistry, vol 346, pp. 147–160, 1988.*

* cited by examiner

*Primary Examiner*—Shailendra Kumar
(74) *Attorney, Agent, or Firm*—James Magee, Jr.

(57) ABSTRACT

The compound 2,4,6-trimethyl-2,4,6-trisila heptane, the preparation thereof, and the use thereof as a silicon carbide precursor in chemical vapor deposition and infiltration procedures are disclosed.

14 Claims, No Drawings

SILICON CARBIDE PRECURSOR

This invention relates to the preparation of advanced ceramic materials and products, particularly to lightweight advanced ceramics having high compressive strength and high hardness. More particularly the invention is directed to carbosilane precursor materials which can be conveniently used to form silicon carbide coatings by vapor deposition at high yields and high purity. The invention includes novel chlorine-free ceramic precursor compositions and methods for making the precursor and vapor phase deposition of silicon carbide coatings. The ceramic precursor compositions can optionally include non reactive constituents such as diluents and carrier gas components. Specifically this invention is directed to 2,4,6-trimethyl-2,4,6-trisilaheptane, the preparation thereof, and the use thereof as a silicon carbide precursor in methods for thermal vapor deposition of silicon carbide on a variety of substrate materials and shapes.

Silicon carbide is a ceramic material which is recognized as useful in a wide variety of applications such as electronics, engine components, low friction bearings, thermal and environmental barrier coatings, wear resistance parts such as brakes and other applications in which high strength, thermal stability, oxidation and corrosion resistance, and low density are required.

Silicon carbide is difficult to process by conventional forming means such as sintering, machining, and spinning. Production of thin films, fibers, composites, and complex shapes of silicon carbide are particularly difficult. Silicon carbide coatings provide a hard, inert surface on a variety of substrate materials and shapes which can be regular, irregular, or complex in geometry.

Carbosilane polymers are known as precursors to silicon carbide ceramics. Illustrative silicon carbide precursors are described in U.S. Pat. No. 5,153,295. These polymers are often referred to as pre-ceramic polymers. To form silicon carbide by chemical vapor deposition, CVD, the precursor composition must be cleanly and easily vaporizable. Many polymers are viscous oils or solids, which can not be easily evaporated even under extreme vacuum. Another common precursor material is methyltrichlorosilane. However the use of this material requires a source of hydrogen gas to combine with the chlorine atoms liberated during decomposition. The reaction forms hydrogen chloride as a by-product which must be removed, thus requiring a scrubber as part of the equipment. Since the hydrogen chloride is corrosive all equipment must be corrosion resistant. Currently available chlorine-free carbosilanes are difficult and costly to produce and often contain excessive amounts of carbon relative to silicon.

Silicon carbide has special utility as a coating material for a wide variety of substrates forms and materials including solid surfaces, two and three dimensional fiber preforms, yarns, felts, woven materials, tube bores, and pre-shaped parts. Coatings can be applied to the substrate by various techniques in which a silicon carbide precursor composition is first applied to the substrate by means such as painting, spraying, and liquid infiltration. The precursor composition is then cured, if necessary, and then pyrolyzed to form the silicon carbide coating. Chemical vapor infiltration and chemical vapor deposition can be used to form coatings of varying thickness from low molecular weight vaporizable precursors in a single step or in multiple incremental steps.

DESCRIPTION OF THE INVENTION

The silicon carbide precursor of this invention is a liquid single chemical compound for deposition of silicon carbide on a variety of substrates and for vapor infiltration of powders, powder compacts, and fiber preforms.

The silicon carbide precursor material of this invention has the following empirical formula $C_7Si_3H_{22}$, named as 2,4,6-trimethyl-2,4,6-trisilaheptane having the following structure:

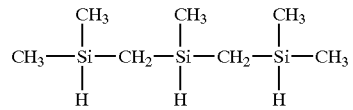

For convenience, the compound which is one of the aspects of this invention may be referred to as TMTSH. This silicon carbide precursor compound may be referred to as SP 2000.

This silicon carbide precursor is a chlorine-free, single compound rather than a polymer, oligomer, or mixture of compounds, oligomers, or reaction products. The main chain of the compound comprises repeating Si—C units. The carbon to silicon ratio in the precursor compound is a relatively low 7:3. This chlorine-free carbosilane contains no elements other than silicon, carbon, and hydrogen and is therefore highly suitable for chemical vapor deposition and chemical vapor infiltration applications. TMTSH provides higher deposition rate and higher yield than can be achieved with methyl-trichlorosilane. Other benefits include ease of preparation, handling, storage, and transportation. The composition is noncorrosive.

The material can be applied to a wide variety of substrate materials and substrate preforms by deposition and infiltration in vapor form to provide an adherent dense coating or matrix of high purity silicon carbide ceramic at high yield.

The chlorine-free feature provides a noncorrosive reaction environment and product. In addition the silicon to carbon (Si:C) ratio is relatively low and can be controlled by control of parameters which affect the deposition rate. Carbon content of the coating can be varied from a slight excess of carbon to near stochiometric ratio of silicon to carbon using nitrogen as a carrier gas. No solvents or reactive secondary gases are required. While a carrier gas is not essential nitrogen, hydrogen, argon, and other suitable carriers can be used to vary flow rates and partial pressure of the TMTSH. Nitrogen, hydrogen, and mixtures thereof are useful for control of stochiometry of the coating.

Carbon content of the coating can be controlled to provide low friction products and articles having desirable thermal and electrical conductivity properties. Thermal decomposition of this silicon carbide precursor compound can be utilized as a practical method for making fine silicon carbide powder in a variety of sizes down to nano sizes.

The following chemical equations illustrate the reactions involved in making the silicon carbide precursor of this invention and will be more clearly understood when considered in conjunction with the examples of this disclosure:

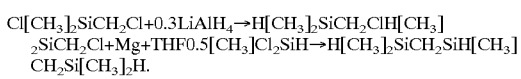

TMTSH is prepared from chloromethyl - dimethylchlorosilane by reduction with lithium aluminum hydride in a suitable solvent such as butyl diglyme (diethylene glycol dibutyl ether) tetrahydrofuran, and other cyclic ethers or acyclic ethers. The resulting chloromethyldimethylsilane is then reacted with magnesium in tetrahydrofuran to form the corresponding Grignard reagent followed by coupling with methyldichlorosilane. The Grignard intermediate need not be isolated. It can be used directly to couple with methyldichlorosilane. The final product, TMTSH, can be recovered by distillation at atmospheric pressure to remove tetrahydrofuran followed by collection at an overhead temperature of about 80° to 85° C. and less than about 20 mm Hg pressure.

Preparation of 2,4,6-trimethyl-2,4,6-trisila-heptane is illustrated in the following examples.

EXAMPLE 1

Synthesis of Chloromethyldimethylsilane

A mixture of 143 g of chloromethyldimethylchlorosilane and 230 g of anhydrous butyl diglyme in a 1 L flask was cooled by an ice-water bath. Then 12 g of lithium aluminum hydride pellets was added to the silane solution. The resultant mixture was stirred in the ice-water bath for 2 h, then heated to 45° C. and kept stirring at this temperature for 20 h. After cooled down to room temperature, the reduced mixture was poured into an ice-water-HCl (10% HCl concentration) solution. The organic layer was separated and dried over anhydrous sodium sulfate ($Na_2SO_4$). Distillation in the temperature range of 80 to 82° C. gave rise to 86 g of chloromethyldimethylsilane.

EXAMPLE 2

Sythesis of 2,4,6-TRIMETHYL-2,4,6-TRISILA-HEPTANE

A solution of 70 g of chloromethyldimethylsilane in 400 ml of anhydrous tetrahydrofuran (THF) was added dropwise to 20 g of magnesium powder in a flask equipped with a mechanical stirrer and a condenser. The rate of addition was regulated to maintain reflux for the Grignard solution. To this Grignard reagent solution was then added dropwise 37 g of methyldichlorosilane in 300 ml THF. The resultant mixture was stirred overnight with gentle reflux. After cooled down to room temperature, the reaction was worked up by adding water. The organic phase was separated and dried over anhydrous sodium sulfate. Solvent (THF) was removed by atmospheric pressure distillation. Vacuum distillation at 85° C./20 mm yielded 56 g of 2,4,6-trimethyl-2,4,6-trisila-heptane.

TMTSH is a colorless liquid organosilane of low viscosity. It is soluble in common organic solvents such as hexane, toluene, tetrahydrofuran, and the like. It is insoluble in water and stable in air.

The compound 2,4,6-trimethyl-2,4,6-trisilaheptane was used as a silicon carbide ceramic precursor in chemical vapor deposition and infiltration procedures. The silicon carbide ceramic can be formed by a variety of thermal or radiation decomposition methods, including pyrolysis, plasma or plasma enhanced treatments, laser heating, electrical arc forming, and anaerobic combustion. The terms "thermal deposition" or "thermal deposition", as used herein include all techniques in which decomposition or reaction of the precursor occurs at temperatures above or at the decomposition temperature of the precursor. The precursor composition can be applied to the substrate by a variety of means such as painting, doping, spraying, and liquid infiltration followed by decomposition to form the silicon carbide coating. When using the vapor method, the vapors are brought into contact with a surface to make a coating or flowed into a fiberous preform to form a matrix. The two techniques are called CVD (chemical vapor deposition) and CVI (chemical vapor infiltration) respectively. The term "surface" as used herein refers to the surface of a substrate on which the coating is to be deposited. The term "substrate" to a body having one or more surfaces on which coatings can be deposited. Bodies include tubes, blocks, fibers, fabrics composed of single fibers or combinations of fibers and other bodies, irregular shaped bodies, and coated surfaces such as carbon coated fibers or other shapes having a coating of carbon or other composition such as a nitride, carbide, boride or the like TMTSH has been used successfully both to deposit coatings on various substrates including single fibers and tows of single fibers and to form a fiberous matrix by infiltrating a fiberous preform such as a 2 or 3 dimensional fabric or felt.

The CVD and CVI coating processes are carried out in a vacuum furnace. The samples to be coated are placed in a vacuum chamber and the chamber is sealed and vacuum is applied to the chamber. Typical vacuum levels are ~1 Torr. When the chamber is under vacuum, it and the substrate are heated to the desired temperature. Deposition temperatures range from about 650° C. to about 1000° C. Once the substrate is hot, the vapors are introduced to the chamber by way of an valve and an evaporator. The particular evaporator used was a heated bubbler with a carrier gas. The bubbler temperature was held at 55° C. for the duration of the run. Other evaporative systems such as ultrasonic nozzles or hot vaporizers can be used. The vapor flows into the chamber, and the molecules decompose and form silicon carbide which deposits onto the substrate. Decomposition products of TMTSH are silicon carbide, methane, and hydrogen. The methane and hydrogen flow away as gas and the coating that remains is substantially pure silicon carbide. Since the precursor is slightly rich in carbon the coating has an elemental carbon content which can impart desirable properties to the coated article.

The deposition conditions can be modified to adjust the composition of the coating which can be varied compositionally from carbon rich to about stoichiometric silicon carbide coatings. The character of the coating formed is variable depending on deposition parameters. Important parameters include the condition such as density, porosity, dryness and cleaning of the deposition surface, partial pressure of the precursor in the reactor, temperature of the target surface, the pressure in the reactor, and the total time of deposition. These parameters influence the deposition rate which has a significant but controllable effect on the structure of the deposited coating.

At lower deposition, about 1 to about 5 microns per hour the coating and is dense and has little or no porosity visible by scanning electron microscope (SEM) measurement at about 4000× (magnification). At higher deposition rates, above 10 microns to millimeters per hour, the coating has porosity and random vertical cracks from top to bottom or partially elongated porosity oriented perpendicular to the deposition surface. Deposition rates of about 60 to about 100 microns per hour provide coatings with highly useful structure. Vertical porosity can be beneficial in some coating applications where integrity is a criteria because the porosity provides the coating with the capability to tolerate a substantial tolerance for differences in thermal expansion with respect to the substrate. The composition of the coating can be varied by the deposition conditions from low porosity to relatively high porosity and from a carbon rich coating to about stoichiometric silicon carbide coating. The ability to control the density and porosity of the silicon carbide deposit provides the ability to deposit multilayer coatings of graduated porosity/density or distinct layers of differing porosity/density on an article or fiber base.

Porosity in silicon carbide coatings on fibers is an important element in durability of fiber matrix bodies. Under stress the capability of the coating to debond from the underlying fiber preserves the physical integrity of the piece.

The chemical vapor infiltration process for matrix formation is carried out in vacuum furnace. The preforms or fabric substrates with open porosity to be infiltrated are placed in the furnace and the chamber sealed. Placement of the target is important, as infiltration depends on the vapors penetrating into the open porosity and contacting the entire surface of all elements of the preform part. Generally in chemical vapor infiltration procedures, it is preferred that the precursor inlet nozzle be in line with the preform to be infiltrated. The vapors leave the inlet nozzle and contact the surfaces of the preform, preferably, within a few inches (1 to 10) to maximize the infiltration efficiency. After the chamber is sealed, the vacuum is applied to the chamber. Typical vacuum levels are about 1 torr. While the chamber is under vacuum, the chamber and the preform within are heated to the desired deposition temperature. This temperature has been investigated from 400° C. to 1000° C. Once the substrate is hot, the precursor vapors are introduced to the chamber by way of a valve and an evaporator. A particular evaporator used was a heated bubbler with a carrier gas inlet. Other devices, such as ultrasonic nozzles or hot vaporizers can be used. Preferably the temperature is held at about 50° C. during the deposition run. The boiling point of TMTSH is about 45° C. at a 1 torr vacuum. The deposition period can be from a few minutes to many hours. Typical infiltration runs are a few hours in length. This compares very favorably to methyltrichlorosilane based SiC infiltration which can take many hundreds of hours. During the run, the vapors flow into the chamber, and the molecules decompose within the substrate. The decomposition products are silicon carbide, methane, and hydrogen. The methane and hydrogen flow away and the matrix that is deposited is primarily silicon carbide. The deposition conditions can be modified such that either a carbon rich or an about stoichiometric silicon carbide coating or matrix is formed on the deposition surface or in the preform.

Both of these coating techniques can be applied to a variety of substrate forms and materials. Typical materials compatible with silicon carbide vapor deposition and infiltration include graphite, silicon, silica (quartz), alumina, zirconia, various carbides (boron, silicon, tungsten, chrome, etc), and other oxide and nitride ceramics. Additionally, TMTSH can be used to coat metals and metal alloys of various types. These include copper, steel, stainless steel, nickel alloys, titanium alloys, aluminum alloys, brass, molybdenum, chromed steel, and the like.

The deposition surface can be in the form of simple and complex shapes such as bars, tubes, crucibles or bowls, I-beams, ceramic foams, and fiber preforms of multi-dimensional structures. Carbon, silicon carbide, mullite, and alumina are illustrative materials for fiber preforms. The fibers themselves can be precoated with compatible thin protective coatings upon which the silicon carbide functional coating can be deposited.

In summary, TMTSH, the compound of this invention, can be used to deposit coatings of silicon carbide on compatible substrates by vapor phase deposition. The substrate inside the hot wall vacuum furnace or reactor is maintained at the desired deposition temperature anywhere between about 600° C. and about 1400° C. Vacuum is maintained between about 1 and 30 torr using, if desired, a non reactive diluent or carrier gas such as hydrogen, nitrogen or argon. Preferred optional carrier gases include hydrogen, nitrogen, argon, and mixtures thereof. The term "non reactive", as used herein, means that the carrier or diluent gas does not react in the chemical reactions which occur during the deposition process. The carrier gas or gases are chemically inert in the thermal decomposition chemistry of the precursor compound in the deposition system. The presence or absence of one or more carrier gases may have an effect on the physical character or chemical composition of the silicon carbide coating, as herein indicated. The boiling point of TMTSH is about 45° C. at 1 torr. It has been established that TMTSH evolves about 50 torr vapor pressure in conjunction with atmospheric pressure nitrogen at about 50° C. Other liquid delivery systems can be used to introduce the TMTSH into the reactor.

The rate of deposit of the coating, speed of coating growth, can be controlled by the flow rate of the precursor composition, TMTSH plus carrier gas if used, through the delivery system, e.g., an evaporator. In general, a higher rate of flow will result in a higher deposition or coating rate. An illustrative high rate of flow is about 20 grams of TMTSH per hour. Generally, higher deposition temperatures of about 1000° C. or above should be used with high flow rates. Chemical vapor infiltration into porous or fibrous preforms is generally carried out at lower rates of flow and lower temperatures, about 700 to about 850° C. compared to deposition on a solid surface.

The present invention will be more thoroughly understood in light of the following working examples of coating experiments.

EXAMPLE 3

TMTSH (SP 2000) was used to coat a ceramic substrate. The composition of the substrate was carbon in the hexagonal crystal form, graphite. An additional substrate of carbon in the cubic crystal form (diamond) was also used. The graphite was in the shape of a flat plate. The diamond was in the form of 100 micron diameter powder. The samples were placed into a vacuum tight quartz reaction tube that was inside of a tube furnace. Twenty grams of TMTSH was added to a bubbler evaporator attached to the quartz tube. The bubbler was equipped with a nitrogen carrier gas inlet. The quartz tube and bubbler system was evacuated by means of a vacuum pump to a pressure of $10^{-3}$ torr. The samples and the reactor were heated to 850° C. using the furnace. The TMTSH silicon carbide precursor was introduced into the reaction tube through the inlet valve. To assist with the vaporization of the TMTSH, the nitrogen carrier gas was turned on to 10 standard cubic centimeters per minute (sccm) and the bubbler was heated to 60° C. During the deposition the system pressure was at 1 torr. All 20 g of the TMTSH was delivered into the reaction tube over the course of one hour. This corresponds to a rate of 20 g/hr or 0.33 g/min. The TMTSH vapors that entered into the reactor decomposed by loss of hydrogen and methane gas to produce a silicon carbide solid. The solid deposited on the surface of the samples. On a flat surface, a flat coating was produced, on the diamond powder, the outside surfaces were evenly coated. The yield per gram of TMTSH is 0.63 g of SiC. Additionally 0 to 0.05 g of carbon was co-deposited due to incomplete loss of methane from the TMTSH.

The amount of the carbon co-deposit is temperature dependent. In this run it was 0.05 g, giving a total yield of 68%. At 800–1000° C. it decreases to below 0.01 g. The coated samples were analyzed by scanning electron microscope/microprobe for morphology and composition. The coating was evenly distributed across the surfaces and the composition was uniform throughout the deposit.

EXAMPLE 4

TMTSH was used to infiltrate ceramic fiber preforms. Three preforms were coated, one of carbon fibers, one of silicon carbide and one of aluminum oxide fibers. The samples were 1"×1"×1" cubes. All samples were placed into a vacuum tight quartz reaction tube that was inside of a tube furnace. One hundred grams of TMTSH was added to a bubbler evaporator attached to the quartz tube. The bubbler was also equipped with a nitrogen carrier gas inlet. The quartz tube and bubbler system was evacuated by means of a vacuum pump to a pressure of $10^{-3}$ torr. The samples and the reactor were heated to 700° C. using the furnace. A bypass gas flow of nitrogen was turned on at 10 times the bubbler flow rate (100 sccm). The silicon carbide precursor (TMTSH) was introduced to the reaction tube through the inlet valve. To assist with the vaporization of the TMTSH, the carrier gas was turned on to 10 sccm and the bubbler was heated to 60° C. During the deposition the system pressure was at 1 torr. All 100 g of the TMTSH was delivered into the reaction tube over the course of three days. This corresponds to a rate of 1.4 g/hr. The TMTSH vapors that flow into the reactor decompose by loss of hydrogen and methane gas to produce a silicon carbide solid. The solid deposits inside of the fiberous samples on the surface of the fibers. This deposit builds up until the spaces between the fibers are filled with the silicon carbide. The yield per gram of TMTSH was 0.63 g of SiC. Additionally 0.05 g of carbon was co-deposited due to incomplete loss of methane from the TMTSH. The infiltrated samples were analyzed by immersion for density and porosity and by scanning electron microscope/microprobe for morphology and composition. The density was evenly distributed throughout the volume and the composition was uniform throughout the deposit.

EXAMPLE 5

TMTSH was used to coat some metal substrates. The substrates were copper, molybdenum, and brass (Cu w/15–30% Zn). The copper was in the form of a pipe 0.5" dia×1" long, the molybdenum was a panel 1"×1"×1/16", and the brass was a cylinder 0.25" dia×0.5" tall. The metals were subjected to an oxidation heat treatment at 900° C. in air for 30 min prior to coating. The samples were placed into a vacuum tight quartz reaction tube that was inside a tube furnace. Twenty grams of TMTSH was added to a bubbler evaporator attached to the quartz tube. The bubbler was also equipped with a nitrogen carrier gas inlet. The quartz tube and bubbler system was evacuated by means of a vacuum pump to a pressure of $10^{-3}$ torr. The samples and the reactor were heated to 900° C. in the furnace. The silicon carbide precursor (TMTSH) was introduced to the reaction tube through the inlet valve. To assist with the vaporization of the TMTSH, the nitrogen carrier gas was turned on to 10 standard cubic centimeters per minute (sccm) and the bubbler was heated to 60° C. During the deposition the system pressure was at 1 torr. All 20 g of the TMTSH was delivered into the reaction tube over the course of one hour. This corresponds to a rate of 20 g/hr or 0.33 g/min. The TMTSH vapors that flow into the reactor decompose by loss of hydrogen and methane gas to produce a silicon carbide solid. This solid deposits in such a way that it matches the surface of the samples. On a flat surface, a flat coating is produced. The yield per gram of TMTSH is 0.63 g of SiC. The coated samples were analyzed by optical microscope for morphology and adhesion. The coating was bumpy and ridged due to the oxide interface layer. The adhesion to the molybdenum was strongest, followed by the copper brass. None of the coatings could be removed by prying with a utility knife.

The silicon carbide precursor compound of this invention is a chlorine free single compound which can be used to deposit near stochiometric coatings of silicon carbide on fibers, flat or irregular surfaces and on the inner surfaces of cylinders or pipe substrates. Coatings having unique physical structure including porosity and cracks normal to the surface can be deposited. This chlorine-free carbosilane contains no elements other than silicon, carbon, and hydrogen and is therefore highly suitable for chemical vapor deposition and chemical vapor infiltration applications. TMTSH provides higher deposition rate and higher yield than can be achieved with methyl-trichlorosilane. Other benefits include ease of preparation, handling, storage, and transportation. The composition is noncorrosive.

What is claimed is:

1. A method for making the silicon carbide ceramic precursor compound, 2,4,6-trimethyl-2,4,6-trisilaheptane, which comprises reducing chloromethyl-dimethylchloro silane with lithium aluminum hydride in a suitable solvent to form chloromethyldimethylsilane; reacting the chloromethyldimethylsilane with magnesium to from the corresponding Grignard reagent; coupling the Grignard reagent with methyldichloro silane; and recovering 2,4,6-trimethyl-2,4,6-trisilaheptane.

2. A process for depositing ceramic silicon carbide on a substrate surface which comprises introducing 2,4,6-trimethyl-2,4,6-trisilaheptane made according to claim 1 into a vacuum furnace which contains the surface upon which silicon carbide is to be deposited, at a furnace temperature of between about 600° C. and about 1400° C. at a pressure of between about $10^{-10}$ torr and about 760 torr for a period of time sufficient to deposit silicon carbide on the substrate.

3. A process according to claim 2 wherein the substrate for deposited silicon carbide is a ceramic.

4. The process according to claim 2 wherein the substrate for silicon carbide deposition is a metal or metal alloy.

5. The process according to claim 2 wherein the substrate for silicon carbide deposition is a single fiber or a two or three dimensional fiber preform.

6. The process according to claim 2 wherein the substrate for silicon carbide deposition is a ceramic or refractory powder.

7. The process according to claim 2 wherein the substrate for silicon carbide deposition is graphite or diamond.

8. A composition for deposition of silicon carbide ceramic by chemical vapor deposition or chemical vapor infiltration comprising the compound 2,4,6-trimethyl-2,4,6-trisilaheptane produced according to claim 1 and an non reactive carrier gas selected from the group consisting of nitrogen, hydrogen, and argon.

9. A process according to claim 2, for depositing ceramic silicon carbide by thermal vapor deposition from a chemical silicon carbide precursor composition comprising 2,4,6-trimethyl-2,4,6-trisilaheptane in vapor form on at least one silicon carbide compatible substrate in a vacuum furnace which contains the surface upon which silicon carbide is to be deposited, at a furnace temperature of between about 700° C. and about 950° C. and at a pressure of between about 0.1 torr and about 200 torr for a period of time sufficient to deposit silicon carbide on the substrate.

10. A process according to claim 9, for depositing ceramic silicon carbide by chemical vapor deposition or chemical vapor infiltration from the silicon carbide precursor 2,4,6-Trimethyl-2,4,6-trisilaheptane in vapor form on at least one silicon carbide compatible surface in a vacuum furnace which contains the substrate upon which silicon carbide is to be deposited, at a furnace temperature of between about 900° C. and about 950° C. and at a pressure of between about 0.1 torr and about 50 torr for a period of time sufficient to deposit silicon carbide on the substrate.

11. A thermal chemical vapor deposited coating of silicon carbide ceramic on a substrate by the process of claim 9, said coating being characterized by the presence of porosity including lines of connected porosity perpendicular to the substrate surface.

12. A silicon carbide ceramic coating deposited by the process according to claim 9 wherein the substrate is a nonfiber preform article having irregular or regular dimensions, a single fiber, or a two or three dimensional fiber preform.

13. A silicon carbide coating deposited according to claim 9 wherein the substrate is a preform of fibers having continuous open porosity.

14. A silicon carbide coating deposited according to claim 9 in which the open porosity is from about 1 to about 99 volume percent of the preform.

* * * * *